(12) United States Patent
Shin et al.

(10) Patent No.: US 8,163,791 B2
(45) Date of Patent: Apr. 24, 2012

(54) IMIDAZOLE DERIVATIVES THAT INDUCE APOPTOSIS AND THEIR THERAPEUTIC USES

(75) Inventors: In-Jae Shin, Goyang (KR); Myung-ryul Lee, Goyang (KR); Darren Williams, Seoul (KR)

(73) Assignee: Industry-Academic Cooperation Foundation, Yonsei University (KR)

( * ) Notice: Subject to any disclaimer, the term of this patent is extended or adjusted under 35 U.S.C. 154(b) by 305 days.

(21) Appl. No.: 12/528,680

(22) PCT Filed: Feb. 26, 2007

(86) PCT No.: PCT/KR2007/000970
§ 371 (c)(1),
(2), (4) Date: Aug. 26, 2009

(87) PCT Pub. No.: WO2008/105565
PCT Pub. Date: Sep. 4, 2008

(65) Prior Publication Data
US 2010/0105726 A1 Apr. 29, 2010

(51) Int. Cl.
*A61K 31/415* (2006.01)
*C07D 233/64* (2006.01)
(52) U.S. Cl. .................... 514/400; 548/338.1
(58) Field of Classification Search .............. 548/338.1; 514/400
See application file for complete search history.

(56) References Cited

U.S. PATENT DOCUMENTS
5,700,826 A 12/1997 Mjalli

FOREIGN PATENT DOCUMENTS
EP 0 812 829 12/1997

OTHER PUBLICATIONS

Ronald C. Rubenstein, et al., "Sodium 4-phenylbutyrate downregulates Hsc70: implications for intracellular trafficking of Delta F508-CFTR"; Am. J. Physiol Cell Physical, 278: C259-C267, 2000.
Bernd Bukau et al., "The Hsp70 and Hsp60 Chaperone Machines" Cell vol. 92, 351-366, Feb. 6, 1998.
Donald D. Newmeyer et al., "Mitochondria: Releasing Power for Life and Unleashing the Machineries of Death", Cell, vol. 112, 481-490, Feb. 21, 2003.
Jean-Pierre Aubry et al., "Annexin V used for Measuring Apoptosis in the Early Events of Cellular Cytotoxicity" Cytometry 37: 197-204, 1999.
Jang-ik Lee et al., "Nuclear Factor Kappa B: Important Transcription Factor and Therapeutic Target", J. Clin. Pharmacol 1998; 38, 981-993.
Ronald C. Rubenstein et al., Sodium 4-phenylbutyrate downregulates HSC70 expression by facilitating mRNA degradation; Am J. Physiol Lung Cell Mol. Physiol, 281: L43-L51, 2001.
David L. Vaus, et al., "Cell Death in Development", Cell vol. 96, 245-254, Jan. 22, 1999.
Ziwei Huang; "The Chemical Biology of Apoptosis: Exploring Protein-Protein Interactions and the Life and Death of Cells with Small Molecules", Chemistry & Biology, vol. 9, 1059-1072, Oct. 2002.
Joerg Hoehfeld et al., "GrpE-like regulation of the Hsc70 chaperone by the anti-apoptotic protein BAG-1", The EMBO Journal, vol. 16, No. 20, pp. 6209-6216, 1997.
Mikkel Rohde et al., "Members of the heat-shock protein 70 family promote cancel cell growth by distinct mechanisms", Genes & Development 19: 570-582, 2005.
Luigi Ravagnan et al., "Heat-shock protein 70 antagonizes apoptosis-inducing factor"; Nature Cell Biology, vol. 3, Sep. 2001, pp. 839-843.
Krieger NR, et al., "Novel immunosuppressants" Pediatric Transplantation 2004: 8: 594-599.
Sue Wickner et al., "Posttranslational Quality Control: Folding, Refolding, and Degrading Proteins" Science, vol. 286, Dec. 3, 1999, pp. 1888-1893.
Karson S. Putt, et al., "Small-molecule activation of procaspase-3 to caspase-3 as a personalized anticancer strategy", Nature Chemical Biology, vol. 2, No. 10, Oct. 2006, pp. 543-550.
Jesper Nylandsted et al., "Selective depletion of heat shock protein 70 (Hsp70) activates a tumor-specific death program that is independent of caspases and bypasses Bcl-2", PNAS, Jul. 5, 2000, vol, 97, No. 14, pp. 7871-7876.
John C. Reed, "Apoptosis-Based Therapies", Nature reviews, vol. 1, Feb. 2002, pp. 111-121.
Craig B. Thompson, "Apoptosis in the Pathogenesis and Treatment of Disease", Science, vol. 267, Mar. 10, 1995, pp. 1456-1462.
Avi Ashkenzai et al., "Death Receptors: Signaling and Modulation", Science, vol. 281, Aug. 28, 1998, pp. 1305-1308.
Mark P. Mattson, "Apoptosis in Neurodegenerative Disorders", Nature Reviews, vol. 1, Oct. 2000, pp. 120-129.
Nancy A. Thornberry et al., "Caspases: Enemies Within", Science, vol. 281, Aug. 28, 1998, pp. 1312-1316.
F. Ulrich Hartl; "Molecular chaperones in cellular protein folding", Nature, vol. 381, Jun. 13, 1996, pp. 571-580.

*Primary Examiner* — Rebecca Anderson
(74) *Attorney, Agent, or Firm* — Cantor Colburn LLP

(57) ABSTRACT

The present invention relates to a pharmaceutical composition comprising compound for induction of apoptosis, a method for inducing cancer cell apoptosis, a method to suppress lymphocyte activation, a method to improve intracellular trafficking of misfolded mutants and a screening method to identify additional compounds useful for inducing apoptosis, and more specifically, it relates to pharmaceutical compositions comprising imidazole derivatives as active gradients for induction of apoptosis to treat various diseases including cancers and immune-related diseases, the method of inducing apoptosis by treating cancer cells with the pharmaceutical composition, the method of inactivating human lymphocytes by treating lymphocytes with the pharmaceutical composition, the method of improving intracellular trafficking of misfolded mutants by treating cells containing the mutants with the pharmaceutical composition, and the screening method for identifying additional compound useful for inducing apoptosis, wherein cells are incubated with the said pharmaceutical composition and detected.

4 Claims, 4 Drawing Sheets

[Fig. 1]

Apoptozole 1

Apoptozole 2

Apoptozole 3

Apoptozole 4

(A) Capan-1 cells (B) CFPAC-1 cells (C)

CFPAC-1 cells
treated with 100 nM Az

IMIDAZOLE DERIVATIVES THAT INDUCE APOPTOSIS AND THEIR THERAPEUTIC USES

TECHNICAL FIELD

The present invention relates to novel compounds that induce apoptosis and pharmaceutical composition including the said compounds. More specifically, it relates to compounds containing an imidazole scaffold that induce apoptosis. In some embodiments, a pharmaceutical composition comprising imidazole derivatives is provided. Furthermore, it relates to the use of the said compounds as therapeutics for treating various medical dysfunctions and diseases, in particular, cancers, immune diseases and cystic fibrosis.

BACKGROUND ART

Apoptosis or programmed cell death is a key process for the normal development and function of multicellular organisms. Damaged or undesired cells in organisms are removed by both the intrinsic apoptotic pathway occurred in mitochondria and the extrinsic apoptotic pathway caused by binding of death ligands (e.g. Fas ligand) to the corresponding receptors (e.g. Fas receptor) (*Cell*, 2003, 112, 481-490 *Science* 1998, 281, 1305-1308 *Cell*, 1999, 96, 245-254). Physiological cell death plays important roles in a wide variety of normal processes, however, aberrant apoptosis causes diverse human diseases (*Science* 1995, 267, 1456-1462 *Nat. Rev. Drug Dis.* 2002, 1, 111-121 *Nat. Rev. Mol. Cell. Biol.* 2000, 1, 120-129). For example, retarded apoptosis contributes to diverse human tumours and the failure to eliminate autoreactive lymphocytes (autoimmunity). In contrast, excessive apoptosis results in neurodegenerative diseases and cardiovascular diseases. Since apoptosis is involved in a wide variety of aforementioned human diseases, research on apoptosis has become one of central areas in biomedical applications. Small molecules that either induce or prevent apoptotic cell death are significantly useful for understanding the mechanisms of action of apoptotic regulatory proteins. In addition, these small molecules can be used as novel therapeutic agents to treat apoptosis-related diseases, such as cancers and autoimmune diseases (*Science* 1995, 267, 1456-1462 *Nat. Rev. Drug Dis.* 2002, 1, 111-121 *Nat. Rev. Mol. Cell. Biol.* 2000, 1, 120-129 *Chem. Biol.* 2002, 9, 1059-1072 *Nat. Chem. Biol.* 2006, 2, 543-550).

Various proteins including Bcl-2 (B cell lymphoma-2) and IAP (inhibitor of apoptosis protein) families are involved in apoptotic pathways. Caspases with aspartate specificity are the main executioner enzymes in apoptotic cell death (*Science* 1998, 281, 1312-1316). Interestingly, chaperone heat shock cognate 70 (Hsc70) suppresses apoptotic cell death by directly associating with apoptosis-inducing factors such as Apaf-1 (*EMBO J.* 1997, 16, 6209-6216 *Nat. Cell. Biol.* 2001, 3, 839-843). Hsc70 plays various roles in cellular processes, such as protein folding of newly synthesized cytoplasmic proteins, refolding of damaged proteins, degradation of misfolded proteins and translocation of cytoplasmic proteins across organellar membranes (*Nature* 1996, 381, 571-579 *Cell* 1998, 92, 351-366 *Science* 1999, 286, 1888-1893). It is known that inhibitors for Hsc70, that induce apoptosis, can be used as anticancer drugs (*Genes Dev.* 2005, 19, 570-582 *Proc. Natl. Acad. Sci. USA* 2000, 97, 7871-7876) and immunosuppressants (*Pediatr Transplant.* 2004, 8, 594-599 *J. Clin. Pharmacol.* 1998, 38, 981-993). Therefore, small molecules that induce apoptotic cell death by inhibiting Hsc70 are useful for both basic biological research to understand the mechanisms of action of apoptotic regulatory proteins and development of novel therapeutic agents to treat apoptosis-related diseases such as cancers and immune-related diseases.

DISCLOSURE OF INVENTION

Technical Problem

Therefore, there is a need in the art for compositions and methods to induce apoptotic cell death using small molecules. The developed small molecules not only provide valuable information on elucidating the molecular mechanism of action of apoptotic regulatory proteins but can also, ultimately, be used as novel therapeutic agents to treat apoptosis-related diseases. The present invention satisfies these and other needs.

Technical Solution

The present invention relates to new compounds and compositions, and methods for inducing apoptosis. Thus, the said compounds and compositions can be used to treat cancer cells and immune-related diseases by inducing apoptosis of cells of interest.

The first object of the present invention is to provide compounds that induce apoptosis.

The second object of the present invention is to provide pharmaceutical compositions comprising compounds inducing apoptosis to treat various diseases including cancers, immune-related diseases and cystic fibrosis. The said compounds include all pharmaceutically acceptable isomers, salts, hydrates, solvates and prodrugs thereof.

The third object of the present invention is to provide methods for inducing apoptosis. When the said compounds are incubated with human cancer cells, they undergo cell death.

The fourth object of the present invention is to provide methods to suppress lymphocyte activation. When the said compounds are incubated with human lymphocytes, they are inactivated by the said compounds.

The fifth object of the present invention is to provide methods to treat cystic fibrosis. When the said compounds are incubated with the cells expressing mutant cystic fibrosis transmembrane regulator (CFTR), the mutant proteins are translocated to cell membranes by said compounds.

The sixth object of the present invention is to provide screening methods to identify additional compounds useful for inducing apoptosis.

Other embodiments of the present invention will become apparent from the following descriptions.

Advantageous Effects

Utilizing the compounds and compositions of this invention, cancer cells and immune-related diseases by inducing apoptosis of cells of interest is able to be treated.

BEST MODE FOR CARRYING OUT THE INVENTION

Figure 1:
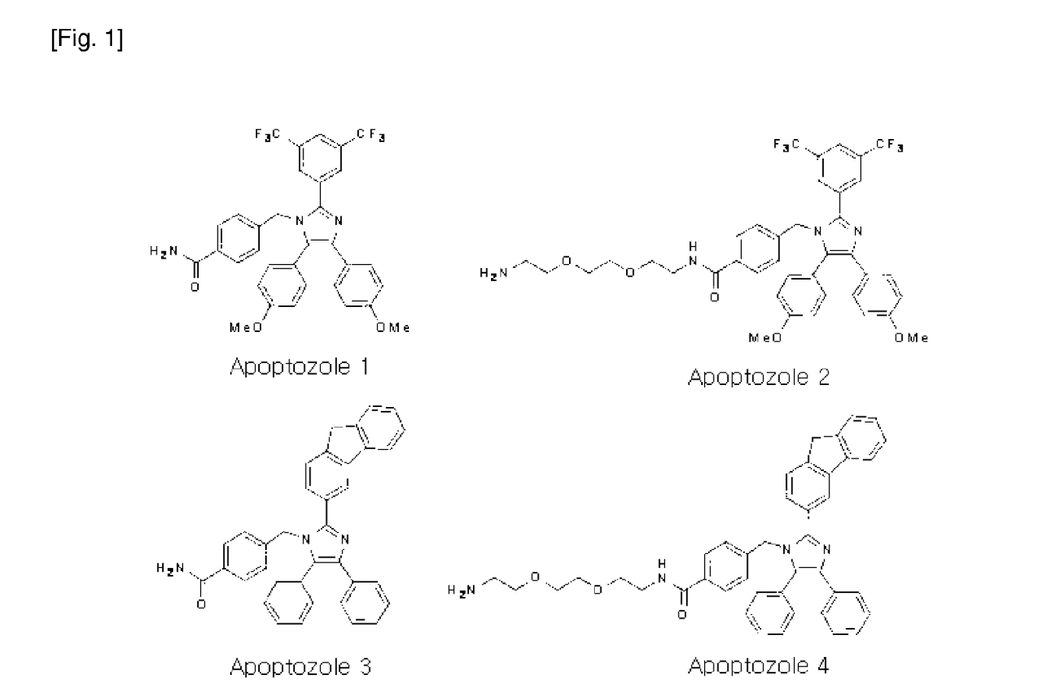
FIG. 1. Structures of Apoptozoles 1-4.

The present invention provides novel imidazole derivatives with the following structures and apoptosis-inducing activity.

The present invention also provides pharmaceutical compositions comprising the imidazole derivatives with Formula (I) as active gradients for induction of apoptosis:

wherein,

$R_1$ is a functional group including, but not limited to, hydrogen, $C_{0-4}$alkylaryl, $C_{1-6}$alkyl, $C_{3-8}$cycloalkyl or $-[(CH_2)_2-O]_{0-3}-(CH_2)_2NH_2$;

$R_2$ is a functional group including, but not limited to, alkyl, $C_{3-8}$cycloalkyl, $C_{0-4}$alkylaryl or alkenylaryl;

$R_3$ is a functional group including, but not limited to, alkyl, $C_{3-8}$cycloalkyl, $C_{0-4}$alkylaryl or alkenylaryl;

$R_4$ is functional group including, but not limited to, alkyl, $C_{3-8}$cycloalkyl, cycloalkyl, $C_{0-4}$alkylaryl or alkenylaryl.

The preferred compounds include derivatives in which $R_1$-$R_4$ groups are functional groups including, but not limited to, the following:

More preferred compounds of the present invention include, but not limited to, the following compounds:

Apoptozole 1

Apoptozole 2

Apoptozole 3

Apoptozole 4

The present invention also provides all pharmaceutically acceptable isomers, salts, hydrates, solvates and prodrugs thereof.

The present invention also provides pharmaceutical compositions comprising the compound described as active gradients for treatment of cancer.

The present invention also provides the method of inducing apoptosis by treating cancer cells with the said compound of the present invention, whereby cancer cells undergo cell death. The method of inducing apoptosis of cancer cells is desirable to comprise further a step of detecting the death of cancer cells, to detect the death of cancer cells is more desirable to measure loss of asymmetry of the phospholipids on the plasma membrane of the said cancer cells.

The present invention also provides pharmaceutical compositions comprising the compound described as active gradients for suppression of lymphocyte activation.

The present invention also provides the method of inactivate human lymphocytes by treating lymphocytes with a compound of the present invention, whereby lymphocytes are inactivated.

The present invention also provides pharmaceutical compositions comprising the compound described as active gradients for treatment of cystic fibrosis.

The present invention also provides the method to improve intracellular trafficking of misfolded mutants by treating cells containing the mutants with a compound of the present invention, whereby the misfolded mutant are translocated to cell membranes.

The present invention also provides the screening method for identifying additional compounds useful for inducing apoptosis, wherein cells are incubated with a compound of the present invention and detected.

Hsc70 that is the Cellular Target Protein of Apoptozoles

Understanding the mode of action of apoptozoles of this invention provides valuable information on mechanisms involved in apoptosis and assists the development of other potent therapeutic agents to treat diseases caused by excessive apoptosis. To investigate the molecular basis of apoptozoles for apoptosis, apoptozole-conjugated agarose matrix is incubated with protein extract from P19 cells and bound proteins are analyzed by SDS/PAGE. One heavy band at 70 kDa is observed after affinity chromatography. When the protein extract is pretreated with external apoptozoles (0.25 and 0.50 mM) as a competitive inhibitor, binding of 70 kDa protein to the Az matrix is mostly prevented, demonstrating specificity for apoptozoles. This band is identified to be heat shock cognate 70 (Hsc70) by nanoLC-MS/MS. To confirm that Hsc70 is a target protein of apoptozoles, Western blot analysis of the protein bound to Az matrix in the presence of external apoptozoles is performed using anti-Hsc70 antibody. Hsc70 is not retained in the presence of apoptozolesas a competitor during affinity chromatography. To further ascertain this result, P19 cells are initially incubated with sodium 4-phenylbutyrate (4-PBA, 0-1.5 mM) that downregulates protein and mRNA expression of Hsc70 by ~40-50% by mRNA degradation, and then the bound protein is assessed by Western blot analysis using anti-Hsc70 antibody. The amount of Hsc70 bound to Az matrix reduces as concentration of 4-PBA increases since P19 cells treated with 4-PBA decreases the amount of Hsc70 available to bind the Az matrix.

The target protein Hsc70 plays various essential roles in cellular processes such as protein folding of newly synthesized cytoplasmic proteins, refolding of damaged proteins, degradation of misfolded proteins, translocation of cytoplasmic proteins across organellar membranes and removal of clathrin from coated vesicles. Since this protein is an anti-apoptotic chaperone protein, Hsc70 is also known to be involved in the development of cancers. Thus, development of anti-tumor agents based on modulation of the cell's propensity to undergo apoptosis by inhibiting this protein is an interesting approach in cancer research. In addition, Hsc70 is a chaperone protein that mediates the nuclear transport of the transcription factors such as NF-kB, which is involved in lymphocyte activation. The uncontrolled activation of NF-kB is suggested to lead to a number of immune and inflammatory diseases, such as allograft rejection, rheumatoid arthritis and bronchial asthma. As a consequence, small molecules that inhibit the function of Hsc70 may be used as immunosuppressive agents for the prevention of transplant rejection and treatment of autoimmune diseases by partially suppressing NF-kB activation. Furthermore, it is also known that Hsc70 assists the degradation of misfolded proteins in the ER. Cystic fibrosis is a disease caused by removal of mutant CFTR (cystic fibrosis transmembrane conductance regulator) in the ER. The most common mutation of CFTR is the deletion of phenylalanine-508 in CFRT ($\Delta$F508-CFRT). This mutant is expressed in the misfolded form, which is retained in the ER by association with Hsc70 for the subsequent degradation by the ubiquitin-proteosome pathway. This leads to the absence of CFTR Cl-channels in the plasma membrane and thus causes abnormal chloride transport in many tissues. It has been reported that inhibition of association of the misfolded mutant CFRT with Hsc70 allows for its exit from the ER and prevents its degradation. This shows that small molecules to transport $\Delta$F508-CFTR to the plasma membrane by inhibiting the function of Hsc70 can be used as therapeutic agents for the treatment of CF caused by CFTR mutation.

Methods for Inducing Apoptosis of Human Cancer Cells by Apoptozoles

Figure 2:
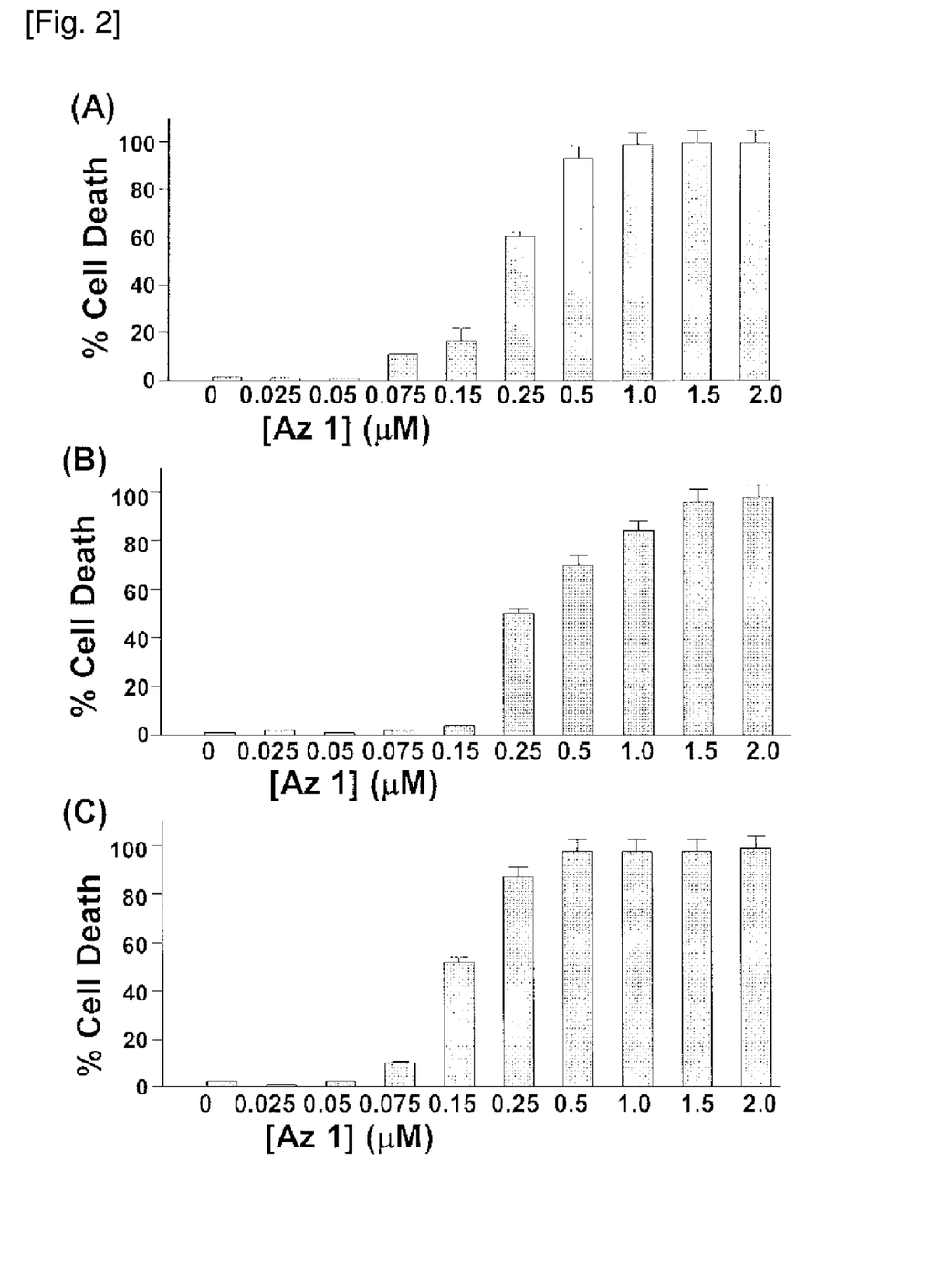
FIG. 2. Apoptotic effect of Az on human cancer cells. Cancer cell lines are incubated with various concentrations of Apoptozole 1 for 6 h and cell death is measured by counting a cell number using CyQuant kit. (A) Ovarian cancer cells (SK-OV-3), (B) colon cancer cells (HCT-15) and (C) lung cancer cells (A549).

One embodiment of the present invention provides methods for inducing apoptosis of cancer cells to treat cancers. In an exemplary embodiment, cancer cells are incubated with a pharmaceutical composition comprising Apoptozoles 1-4, and undergo cell death. Human cancer cells (ovarian cancer cells; SK-OV-3, colon cancer cells; HCT-15, lung cancer cells; A549) are incubated with various concentrations of a compound of Formula I (or a composition thereof), whereupon the cells undergo apoptotic cell death. The concentration of a compound of Formula I, such as Apoptozoles 1-4, can be adjusted to induce apoptosis of cancer cells. Typically, Apoptozoles 1-4 are incubated with the cancer cells between 0.05 µM to 1.0 µM.

HCT-15 human colorectal adenocarcinoma cells and SK-OV-3 human ovary adenocarcinoma cells are cultured in RPMI 1640 medium supplemented with 10% FBS. A549 human lung carcinoma cells are cultured in Ham's F12K medium supplemented with 10% FBS. The culture media for all cell lines contain 4 mM L-glutamine and supplemented with 100 units/mL penicillin and 100 μg/mL streptomycin. Cancer cells are cultured under conditions known to be optimal for cell growth. Such conditions include a temperature of 37° C. with 5% $CO_2$ in air atmosphere. Cells are cultured on plastic dishes, flasks, or roller bottles according to the methods of the present invention. Suitable culture vessels include multi-well plates, Petri dishes, tissue culture tubes, flasks, roller bottles, and so on.

Apoptotic cell death is measured by the use of the combination of FITC-annexin V (2 μg/mL) and propidium iodide (PI, 5 μg/mL) (*Cytometry* 1999, 37, 197-204). The apoptotic process is a relatively fast event (2-4 h) and includes loss of asymmetry of the phospholipids on the plasma membrane, leading to the exposure of phosphatidylserine on the outer surface. The exposed phosphatidylserine is detected by FITC-annexin V. PI is used to detect membrane perturbed cells (late apoptosis and membrane permeabilization, a feature of the early stage of necrosis) rather than apoptosis. Thus, compounds that show positive annexin V staining and negative PI staining in P19 cells are selected. Furthermore, cell proliferation is determined by using the CyQuant Cell Proliferation Assay Kit (Invitrogen).

Methods of Screening Compounds that Induce Apoptosis

Another embodiment of the present invention provides a screening method for additional compounds that induce apoptosis. Cells are incubated with a test compound that may possess the potential to induce apoptosis. Cell death can be detected by the use of the combination of FITC-annexin V (2 μg/mL) and propidium iodide (PI, 5 μg/mL) (*Cytometry* 1999, 37, 197-204) and cell number is counted by using the CyQuant Cell Proliferation Assay Kit (Invitrogen). The test compound that induces apoptosis is identified as a "hit".

In one preferred embodiment, high-throughput screening methods involve providing a library containing a large number of potential therapeutic compounds. Such combinatorial chemical libraries are then screened in one or more assays to identify those library members that display apoptosis-inducing activity. The compounds thus identified can serve as conventional lead compounds or can be used as potential or actual therapeutics.

Inactivation of Human Lymphocytes by Apoptozoles

The other embodiment of the present invention provides methods of inactivating human lymphocytes to treat immune-related diseases. In this embodiment, lymphocytes are incubated with a compound of Formula I (or a composition thereof), whereupon the lymphocytes are inactivated. Hsc70 that is a target protein of Apoptozoles is a chaperone protein that mediates the nuclear transport of the transcription factors such as NF-kB, which is involved in lymphocyte activation. The uncontrolled activation of NF-kB is suggested to lead to a number of immune and inflammatory diseases, such as allograft rejection, rheumatoid arthritis and bronchial asthma (*Pediatr Transplant.* 2004, 8, 594-599 *J. Clin. Pharmacol.* 1998, 38, 981-993). As a consequence, small molecules that inhibit the function of Hsc70 may be used as immunosuppressive agents for the prevention of transplant rejection and treatment of autoimmune diseases by partially suppressing NF-kB activation.

Figure 3:
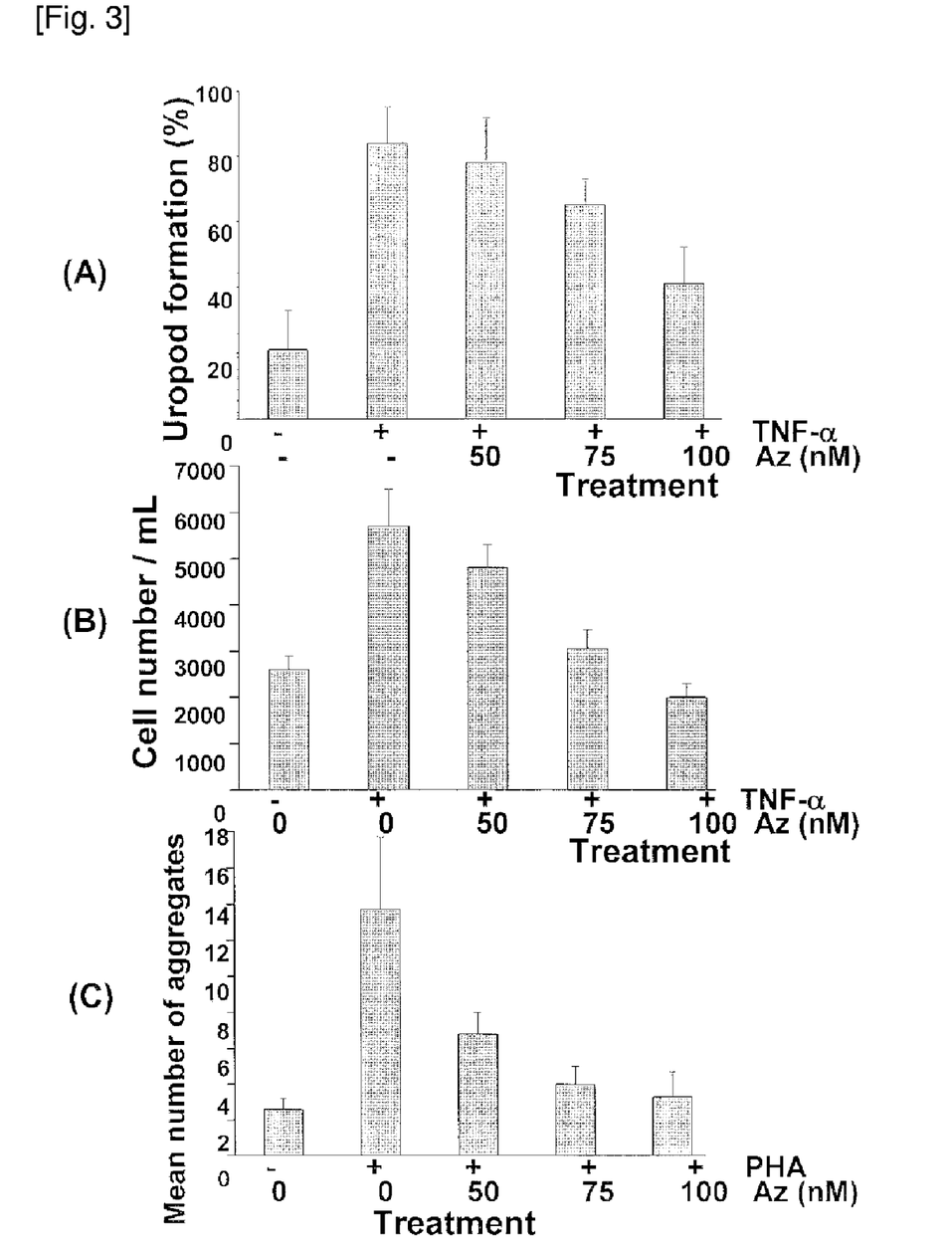
FIG. 3. Suppression of TNF-α and PHA-induced human lymphocyte activation by Apoptozole 1. (A) Jurkat human lymphocytes are treated with various concentrations of Apoptozole 1 for 1 h and then are activated by incubation with 10 ng/mL of TNF-α for 1 h to induce uropod formation. The formed uropod is determined by microscopic analysis of groups of cells. (B) Lymphocytes treated with TNF-α (10 ng/mL) for 48 h are incubated with various concentrations of Apoptozole 1 for 24 h. Cell number is measured by CyQuant kit. (C) Jurkat human lymphocytes are incubated with various concentrations of Apoptozole 1 for 1 h and then with 10 μg/mL PHA for 1 h to induce cell aggregation. Cell aggregates are counted in 40× fields of view determined randomly.

Lymphocyte activation leads to the formation of a uropod in the rear pole during cell polarization and cell proliferation. Jurkat lymphocytes are incubated with various concentrations of Apoptozoles for 1 h and the treated cells are then activated by treatment with TNF-α for 1 h. Apoptozoles reduce the uropod formation induced by TNF-α by 45% in comparison with cells treated only with TNF-α. Apotozoles also suppress T cell proliferation induced by TNF-α (65% reduction of proliferation by 100 nM Apoptozoles). Furthermore, Apoptozoles suppress the homotypic aggregation in lymphocytes induced by phytohemagglutinin (PHA). Jurkat lymphocytes are treated with various concentrations of Apoptozoles for 1 h and then with PHA for 1 h to induce homotypic aggregation. Apoptozoles suppress lymphocyte aggregation (76% reduction of aggregation by 100 nM Apoptozoles).

Translocation of Mutant CFTR to Plasma Membranes by Apoptozoles

Figure 4:
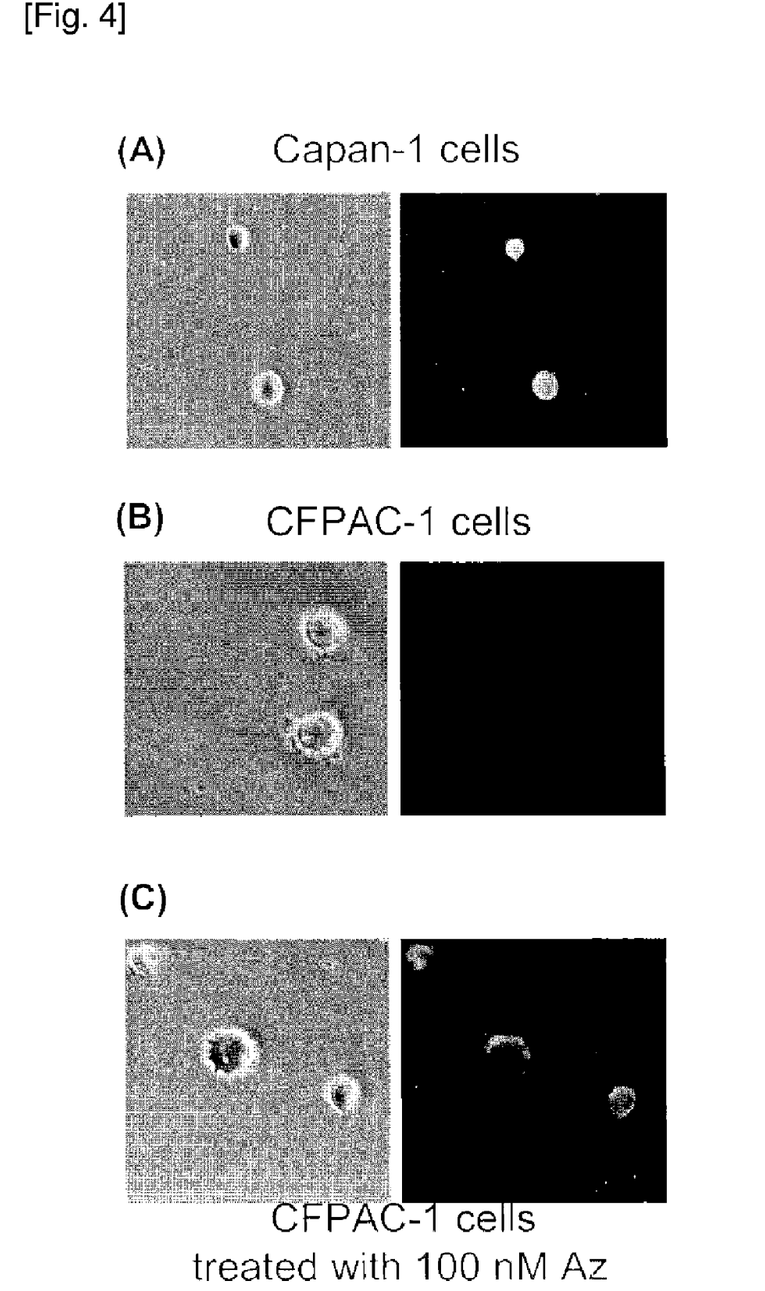
FIG. 4. Intracellular trafficking of misfolded ΔF508-CFTR by Apoptozole 1. (A) Capan-1 cells expressing normal CFTR display intense fluorescence in a characteristic ring structure that is indicative of cell membrane labeling. (B) CFPAC-1 cells expressing ΔF508-CFTR show little or no fluorescent signal at the cell surface, due to degradation ΔF508-CFTR by interacting with Hsc70 in the proteosome pathway. (C) CFPAC-1 cells treated with a sub-apoptotic inducing concentration of Apoptozole 1 (100 nM) for 24 h inhibits Hsc70-mediated degradation of the ΔF508-CFTR (left: microscopic images, right: fluorescence images after immunostaining). Immunostaining for CFTR is carried out using standard methods without cell permeabilization to allow CFTR detection on the cell surface.

The other embodiment of the present invention provides translocation methods of mutant CFTR (cystic fibrosis transmembrane conductance regulator) to treat cystic fibrosis. Hsc70 assists the degradation of misfolded proteins in the ER (*Nature* 1996, 381, 571-579 *Cell* 1998, 92, 351-366 *Science* 1999, 286, 1888-1893). Cystic fibrosis is a disease caused by removal of mutant CFTR in the ER. The most common mutation of CFTR is the deletion of phenylalanine-508 in CFRT (ΔF508-CFRT). This mutant is expressed in the misfolded form, which is retained in the ER by association with Hsc70 for the subsequent degradation by the ubiquitin-proteosome pathway. This leads to the absence of CFTR Cl⁻ channels in the plasma membrane and thus causes abnormal chloride transport in many tissues. It has been reported that inhibition of association of the misfolded mutant CFRT with Hsc70 allows for its exit from the ER and prevents its degradation (*Am. J. Physiol. Lung Cell Mol. Physiol.* 2001, 281, L43-L. *Am. J. Physiol. Cell Physiol.* 2000, 278, C259-C267). This shows that small molecules to transport ΔF508-CFTR to the plasma membrane by inhibiting the function of Hsc70 can be used as therapeutic agents for the treatment of CF caused by CFTR mutation. To examine the potential of Apoptozoles for enhancing the intracellular trafficking of mutant ΔF508-CFTR to plasma membrane, two cell lines, Capan-1 and CFPAC-1, are used for these studies. Non-permeabilized Capan-1 cells express normal CFTR in cell membrane. Non-permeabilized CFPAC-1 cells, a pancreatic duct cell line derived from a patient with CF bearing ΔF508 mutation, express mutant ΔF508-CFTR and display little or no protein at the cell surface, due to proteolytic degradation of ΔF508-CFTR in the proteosome pathway. When Capan-1 cells are immunostained with anti-CFTR antibody, intense fluorescence is observed in the cell membrane. In contrast, immunostained CFPAC-1 cells show little or no fluorescent signal at the cell surface due to intracellular degradation of the mutant CFTR. However, CFPAC-1 cells, after 24 h treatment with 100 nM Apoptozoles (a concentration that does not induce apoptosis), express a portion of the ΔF508-CFTR on the cell membrane by escaping degradation mediated by the chaperone function Hsc70.

Methods of Treatment

Another embodiment of the invention provides methods of treating individuals with diseases or disorders which can be treated by administration of Apoptozoles. In this embodiment, individuals in need of such treatment are treated with a compound of Formula I (e.g. Apoptozoles 1-4 or compositions thereof), whereupon cancer cells undergo apoptosis, lymphocytes are inactivated or mutant CFTR is expressed on the cell membrane.

The following examples are offered to illustrate, but not limited to, the claimed invention.

Example 1

Synthesis of 4-2-[3,5-bis(trifluoromethyl)phenyl]-4, 5-bis(4-methoxphenyl)imidazol-1-yl-methyl-benzamide (Apoptozole 1)

Apoptozole 1

To a stirred solution of ammonium acetate (0.6 g, 8.0 mmol) in acetic acid (5 mL) was added 3,5-bis(trifluoromethyl)benzaldehyde (0.3 μL, 1.7 mmol), 4,4'-dimethoxybenzil (0.5 g, 1.7 mmol) and 4-(aminomethyl)benzamide (0.2 g, 1.3 mmol) at 100° C. After stirring for 5 h, the reaction mixture was diluted with $CH_2Cl_2$ and washed with $H_2O$ and brine. The organic layer was dried over anhydrous $MgSO_4$, filtered and concentrated under the reduced pressure. The crude product was purified by flash column chromatography (3:1 to 1:1 hexane/EtOAc) to give a pure product (0.4 mmol, 30%): $^1$H NMR (250 MHz, $CD_3OD$) δ 8.82 (s, 2 H), 8.67 (s, 2 H), 8.40 (d, 2 H, J=10.0), 8.06 (d, 2 H, J=8.8), 7.90 (d, 2 H, J=8.1), 7.62-7.58 (m, 4 H), 7.45 (d, 2 H, J=8.8), 5.91 (s, 2 H), 4.45 (s, 3 H), 4.40 (s, 3 H) $^{13}$C NMR (125 MHz, $CD_3OD$) δ 171.6, 162.0, 160.5, 145.9, 142.4, 140.1, 134.5, 134.3, 133.7, 133.4, 133.2, 132.5, 130.4, 129.6, 129.4, 127.6, 127.2, 123.7, 123.1, 115.8, 114.8, 55.9, 55.8, 40.5 MALDI-TOF-MS calcd for $C_{33}H_{25}F_6N_3O_3$ (M+Na)$^+$648.18, found 648.18.

Example 2

Synthesis of N-2-[2-(2-aminoethoxy)ethoxy]ethyl-4-2-[3,5-bis(trifluoromethyl)phenyl]-4,5-bis(4-methoxy-phenyl)imidazol-1-yl-methyl]-benzamide (Apoptozole 2)

-continued

Apoptozole 2

To a stirred solution of ammonium acetate (0.9 g, 11.9 mmol) in acetic acid (5 mL) was added 3,5-bis(trifluoromethyl)benzaldehyde (0.4 μL, 2.6 mmol), 4,4'-dimethoxybenzil (0.7 g, 2.6 mmol) and 4-(aminomethyl)benzoic acid (0.3 g, 2.0 mmol) at 100° C. After stirring for 5 h, the volatile material was removed under the reduced pressure. Water was added to the residual oil to obtain a crude solid. The solid was collected by filtration and then washed with ether several times to give a pure acid (0.6 mmol, 32%): $^1$H NMR (250 MHz, DMSO-$d_6$) δ 8.18 (s, 2 H), 8.13 (s, 2 H), 7.79 (d, 2 H, J=8.2), 7.42 (d, 2 H, J=8.7), 7.29 (d, 2 H, J=8.6), 7.02 (d, 2 H, J=8.6) 6.83 (d, 4 H, J=8.8), 5.26 (s, 2 H), 4.45 (s, 3 H), 3.78 (s, 3 H) $^{13}$C NMR (62.5 MHz, DMSO-$d_6$) δ 176.4, 169.3, 167.7, 152.9, 151.5, 147.2, 142.6, 141.8, 140.5, 140.2, 139.9, 139.4, 139.3, 138.0, 137.0, 136.3, 135.5, 134.8, 131.4, 124.3, 123.3, 64.7, 64.6, 24.7; MALDI-TOF-MS calcd for $C_{33}H_{24}F_6N_2O_4$ (M+Na)$^+$ 649.15. found 649.16.

A solution of acid (50.1 mg, 80 mmol) obtained from above procedure, 1-benzotriazolyloxytris(dimethylamino)phosphonium hexafluorophosphate (BOP, 53.0 mg, 120 mmol), 1-hydroxybenzotriazole (HOBt, 16.2 mg, 120 mmol) and N-ethylmorpholine (NEM, 15.2 mL, 120 mmol) in DMF (500 μL) was added to aminoethylated Wang resin (0.04 g, 40 mmol). After 12 h shaking, the resin was washed with DMF several times. The coupled resin was reacted with TFA-TES (90:10) for 1 h to release a product. The crude product was purified by preparative RP-HPLC with a gradient 2-100% $CH_3CN$ in water over 90 min: $^1$H NMR (400 MHz, $CD_3OD$) δ 8.17 (s. 2 H), 8.07 (s, 2 H), 7.70 (d, 2 H, J=8.4), 7.40 (d, 2 H, J=8.8), 7.25 (d, 2 H, J=8.8), 6.96 (d, 2 H, J=8.8), 6.81 (d, 2 H, J=9.2), 5.27 (s, 2 H), 3.80 (s, 3 H), 3.75 (s, 3 H), 3.68-3.63 (m, 8 H), 3.54 (t, 2 H, J=5.6), 3.08 (t, 2 H, J=5.2) $^{13}$C NMR (125 MHz, $CD_3OD$) δ 169.6, 162.1, 160.7, 145.6, 141.9, 139.4, 135.1, 133.7, 133.6, 133.5, 133.2, 132.5, 130.5, 129.7, 129.0, 127.3, 126.8, 124.0, 122.7, 115.8, 114.9, 71.5, 71.4, 70.7, 68.0, 55.9, 55.8, 40.8, 40.7; MALDI-TOF-MS calcd for $C_{39}H_{38}F_6N_4O_5$ (M+Na)$^+$ 779.26, found 779.27.

Using the procedures described in Examples 1-2 above and the appropriate starting materials and reagents, the following imidazole derivatives are also prepared:

4-[2-(9H-Fluoren-3-yl)-4,5-diphenylimidazol-1-yl-methyl]benzamide (Apoptozole 3) and N-2-[2-(2-aminoethoxy)ethoxy]ethyl-4-[2-(9H-fluoren-3-yl)-4,5-diphenylimidazol-1-yl-methyl]benzamide (Apoptozole 4).

Example 3

Cell Culture and Small Molecule Screening

Jurkat human lymphocytes are cultured in RPMI 1640 medium supplemented with 5% FBS. HCT-15 human colorectal adenocarcinoma cells and SK-OV-3 human ovary adenocarcinoma cells are cultured in RPMI 1640 medium supplemented with 10% FBS. A549 human lung carcinoma cells are cultured in Ham's F12K medium supplemented with 10% FBS. The culture media for all cell lines contain 4 mM L-glutamine and supplemented with 100 units/mL penicillin and 100 mg/mL streptomycin. All the cells are cultured at 37° C. and 5% $CO_2$.

For small molecule screen, an imidazole derivatives are screened in parallel 96-well plates, one plate used for measuring phosphatidylserine exposed to the cell membrane during apoptosis (via FITC-annexin V labeling of the cell membrane) and one plate used for measuring cell membrane permeabilization (via propidium iodide labeling of the cell nucleus). Each compound is added to duplicate wells of a 96-well tissue culture plate containing 5×10$^4$ P19 cells at a final concentration of 500 nM. As a positive control, duplicate wells are incubated with 500 μM hydrogen peroxide for 3 h to induce apoptosis. Cells treated with 0.1% DMSO alone are used as a negative control. Cells are incubated with each compound for 3 h and then washed with PBS twice. After fixation of the incubated cells with 3% formaldehyde in PBS for 10 min at room temperature, the fixed cells are washed with PBS twice. Cell cultures in one 96-well plate are incubated with dilution FITC-annexin V (2 μg/mL) and ones in the second plate are treated with PI (5 μg/mL). Both plates are incubated for 5 min in the dark. Cell cultures are washed with PBS three times and fluorescence intensity is quantified using a fluorescence microplate reader (SpectraMax GeminiEM, Molecular Devices). The FITC-annexin signal is read at 485 nm excitation and 538 nm emission. The PI signal is read at 544 nm excitation and 612 nm emission. Compounds that show positive FITC-annexin V and negative PI are selected as "hit compounds" that induce apoptosis.

Example 4

Cell Proliferation and Survival Assay

Cells are plated in a 96-well plate at 10$^5$ cells/mL and cultured for 48 h in complete growth medium. The cells are treated with Apoptozoles for 6 h and then the cells are cultured with drug-free medium. Cells are harvested by trypsinization to eliminate dead cells from the sample. Cell proliferation is determined by the CyQuant Cell Proliferation Assay Kit (Invitrogen).

Example 5

Suppression of Lymphocyte Activation

Jurkat human lymphocytes are seeded in 6-well plates at a density of 103 cells/mL in 5% FBS in order to reduce the propensity for spontaneous uropod formation. Lymphocytes are treated with various concentrations (0-100 μM) of Az for 1 h. Az-treated lymphocytes are activated by incubation with TNF-α (10 ng/mL) for 1 h to induce uropod formation. The formed uropod is determined by microscopic analysis of groups of cells.

For homotypic aggregation studies, lymphocytes are seeded in 6-well plates at a density of 2×10$^4$ cells/mL and treated with various concentrations (0-100 nM) of Az for 1 h. Cells are then incubated with 10 μg/mL of PHA for 1 h to induce cell aggregation. Cell aggregates are counted in 40× fields of view determined randomly.

Example 6

Detection of ΔF508-CFTR Expression on the Cell Membrane

Capan-1 and CFPAC-1 cells are grown on Permanox slides (Fisher Scientific) for 24 h and treated with 1 mM 4-PBA and 100 nM Az for 24 h. The treated cells are washed three times with warm PBS. Immunostaining using CFTR rabbit polyclonal (1:500, Abcam), biotin-conjugated anti-rabbit (1:500, Abcam) and Texas Red-conjugated streptavidin is carried out on cell suspensions using standard procedure, omitting Triton X-100 from the fixation solution to allow CFTR detection on the cell surface. The slides were analyzed using a fluorescence microscope (Nikon Eclipse TE2000).

The invention claimed is:

1. A compound being a member selected from the group consisting of the following structures:

Apoptozole 1

Apoptozole 2

2. A pharmaceutical composition comprising the compound selected from the group of the following structures:

Apoptozole 1

Apoptozole 2

3. A pharmaceutical composition comprising the compound of claim 2 for the treatment of ovarian cancer, colon cancer or lung cancer.

4. A pharmaceutical composition comprising the compound of claim 2 for treatment of cystic fibrosis.

* * * * *